United States Patent
Hirokawa

(10) Patent No.: US 12,020,503 B2
(45) Date of Patent: Jun. 25, 2024

(54) FINGERPRINT PROCESSING DEVICE, FINGERPRINT PROCESSING METHOD, PROGRAM, AND FINGERPRINT PROCESSING CIRCUIT

(71) Applicant: NEC Corporation, Tokyo (JP)

(72) Inventor: Akira Hirokawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 18/121,880

(22) Filed: Mar. 15, 2023

(65) Prior Publication Data

US 2023/0222831 A1  Jul. 13, 2023

Related U.S. Application Data

(63) Continuation of application No. 17/162,116, filed on Jan. 29, 2021, now Pat. No. 11,631,274, which is a continuation of application No. 16/342,705, filed as application No. PCT/JP2017/033041 on Sep. 13, 2017, now Pat. No. 10,936,849.

(30) Foreign Application Priority Data

Oct. 19, 2016 (JP) ................... 2016-204835

(51) Int. Cl.
*G06V 40/12* (2022.01)
*A61B 5/1172* (2016.01)
*G06T 7/00* (2017.01)

(52) U.S. Cl.
CPC ........ *G06V 40/1376* (2022.01); *A61B 5/1172* (2013.01); *G06T 7/00* (2013.01); *G06V 40/1347* (2022.01); *G06V 40/1359* (2022.01); *G06V 40/1365* (2022.01)

(58) Field of Classification Search
CPC .... G06K 9/00013; G06K 9/0004; G06K 7/14; G06K 9/0002; G06F 2203/0338; G06F 2203/04111; G06F 2203/04112
See application file for complete search history.

(56) References Cited

U.S. PATENT DOCUMENTS 6,041,133 A    3/2000  Califano et al.
6,072,895 A *  6/2000  Bolle ................. G06V 40/1347
                                                   382/209

(Continued)

FOREIGN PATENT DOCUMENTS

JP     4-098468 A     3/1992
JP     H07-057092 A   3/1995

(Continued)

OTHER PUBLICATIONS

International Search Report for PCT/JP2017/033041 dated Oct. 24, 2017 (PCT/ISA/210).

(Continued)

*Primary Examiner* — Yuzhen Shen

(57) ABSTRACT

A fingerprint processing device includes a match processing unit configured to determine, based on a first degree, a plurality of feature points having a large value of the first degree among the feature points of a fingerprint specified in a fingerprint image of a matching source, the first degree representing a first distance to other feature points, as representative feature points used in match processing of the fingerprint.

8 Claims, 12 Drawing Sheets

(56) References Cited

U.S. PATENT DOCUMENTS

| | | | |
|---|---|---|---|
| 6,233,348 B1 | 5/2001 | Fujii | G06V 40/1365 382/125 |
| 2001/0031075 A1 | 10/2001 | Fujii | |
| 2003/0075985 A1 | 4/2003 | Moghaddam | G06V 40/1365 382/124 |
| 2007/0036400 A1 | 2/2007 | Watanabe et al. | |
| 2009/0245596 A1 | 10/2009 | Niinuma | |
| 2011/0001607 A1 | 1/2011 | Kamakura | |
| 2012/0150450 A1 | 6/2012 | Monden | |
| 2014/0016834 A1* | 1/2014 | Endoh | G06V 40/10 382/115 |
| 2015/0193665 A1 | 7/2015 | Fukuda | G06V 10/42 382/115 |

FOREIGN PATENT DOCUMENTS

| | | | | |
|---|---|---|---|---|
| JP | H0757092 A | * | 3/1995 | G06F 15/62 |
| JP | 10-177650 A | | 6/1998 | |
| JP | 2001-307102 A | | 11/2001 | |
| JP | 2001-344604 A | | 12/2001 | |
| JP | 2005-346518 A | | 12/2005 | |
| JP | 2006-012080 A | | 1/2006 | |
| JP | 2006-277146 A | | 10/2006 | |
| JP | 2007-328502 A | | 12/2007 | |
| JP | 2011-141744 A | | 7/2011 | |
| JP | 5822303 B2 | | 11/2015 | |
| JP | 2015-228070 A | | 12/2015 | |
| WO | 2010/119500 A1 | | 10/2010 | |
| WO | 2012/127630 A1 | | 9/2012 | |

OTHER PUBLICATIONS

Communication dated Aug. 22, 2019, from the European Patent Office in counterpart European Application No. 17862903.5.
Notice of Allowance dated Oct. 29, 2020, issued by the USPTO in U.S. Appl. No. 16/342,705.
Office Action Non-Final dated Jun. 8, 2020, issued by the USPTO in U.S. Appl. No. 16/342,705.
Japanese Office Action for JP Application No. 2020-188189 dated Nov. 9, 2021 with English Translation.
Takahiro Nakamura et al., "Fingerprint Verification using Reliability Evaluation of Non-matching Minutiae", IEICE Technical Report, Japan, the Institute of Electronics, Information and Communication Engineers, Mar. 10, 2006, vol. 105, No. 674, pp. 167-172.
Japanese Office Communication for JP Application No. 2022-026934 dated Jan. 31, 2023 with English Translation.
U.S. Office Action for U.S. Appl. No. 17/162,116 dated Aug. 18, 2022.
U.S. Notice of Allowance for U.S. Appl. No. 17/162,116 dated Dec. 16, 2022.
U.S. Corrected Notice of Allowance for U.S. Appl. No. 17/162,116 dated Mar. 7, 2023.

* cited by examiner

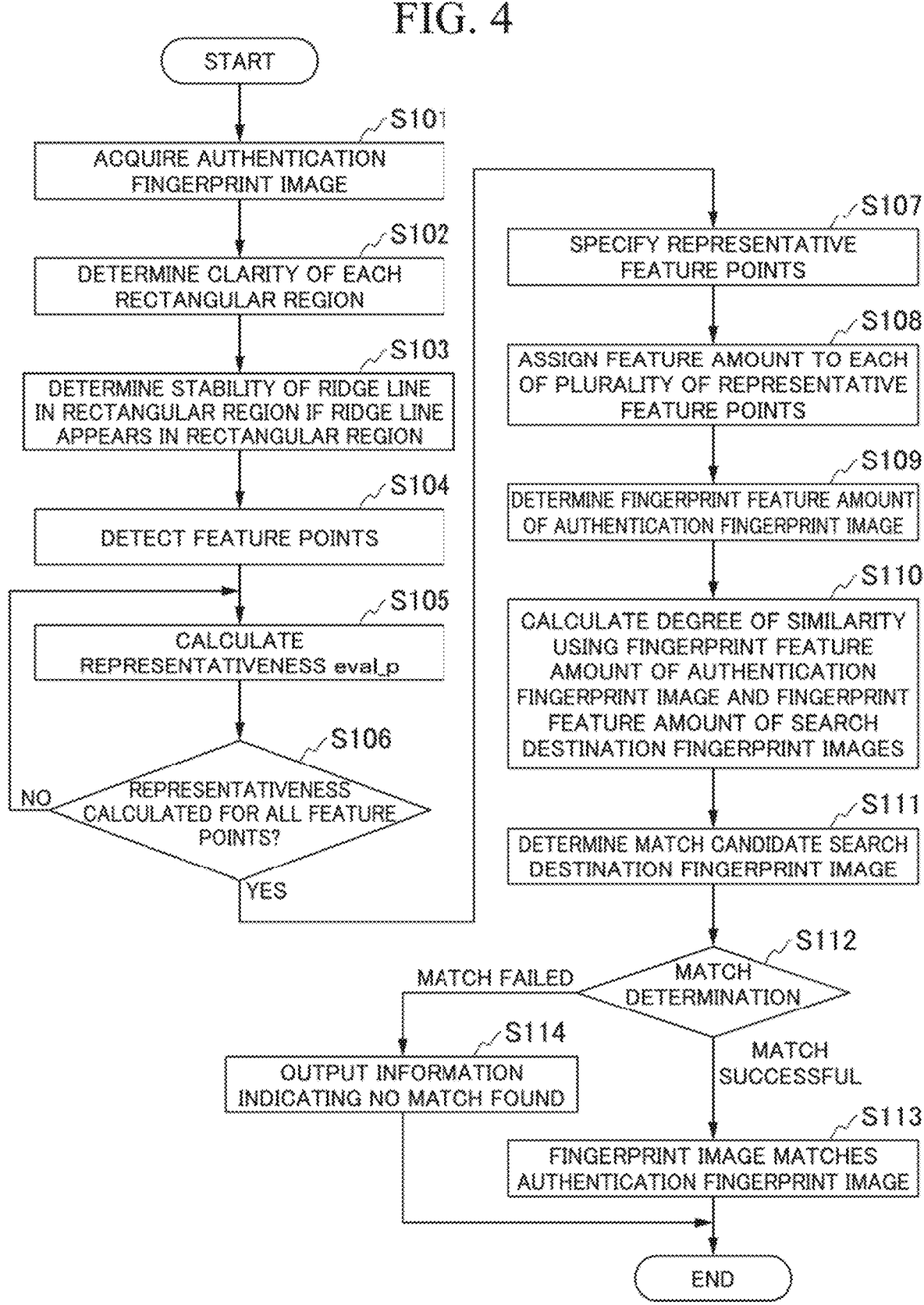

FINGERPRINT PROCESSING DEVICE, FINGERPRINT PROCESSING METHOD, PROGRAM, AND FINGERPRINT PROCESSING CIRCUIT

CROSS REFERENCE TO RELATED APPLICATIONS

This application is a Continuation of U.S. patent application Ser. No. 17/162,116 filed Jan. 29, 2021, which is a Continuation of U.S. patent application Ser. No. 16/342,705 filed Apr. 17, 2019, which issued as U.S. Pat. No. 10,936,849, which is a National Stage of International Application No. PCT/JP2017/033041 filed Sep. 13, 2017, claiming priority based on Japanese Patent Application No. 2016-204835, filed Oct. 19, 2016, the disclosure of which is incorporated herein in its entirety.

TECHNICAL FIELD

The present invention relates to a fingerprint processing device, a fingerprint processing method, a program, and a fingerprint processing circuit.

BACKGROUND ART

When performing fingerprint matching, for example, the center (core) of a fingerprint is calculated from a fingerprint image, and matching between an image of a fingerprint matching source and a fingerprint matching destination is carried out using information such as the position of feature points referenced to the center thereof. However, if the position of the center of the fingerprint in the fingerprint image is incorrectly specified, a deviation results in the relationship between the center of the fingerprint and the feature point, thereby diminishing the accuracy of matching. Techniques related to fingerprint matching are disclosed in Patent Documents 1 to 3.

CITATION LIST

Patent Literature

[Patent Document 1] Japanese Unexamined Patent Application, First Publication No. Hei 10-177650
[Patent Document 2] Japanese Unexamined Patent Application, First Publication No. 2015-228070
[Patent Document 3] Japanese Patent (Granted) Publication No. 5,822,303

SUMMARY OF INVENTION

Problems to be Solved by the Invention

As a result of the problem mentioned above, a fingerprint processing device that performs fingerprint matching without specifying the center of a fingerprint and has a fast matching speed is required.

Therefore, the present invention has an object of providing a fingerprint processing device, a fingerprint processing method, a program, and a fingerprint processing circuit that solve the problem mentioned above.

Means for Solving the Problem

According to a first aspect of the present invention, a fingerprint processing device includes a match processing unit configured to determine, based on a first degree, a plurality of feature points having a large value of the first degree among the feature points of a fingerprint specified in a fingerprint image of a matching source, the first degree representing a first distance to other feature points, as representative feature points used in match processing of the fingerprint.

According to a second aspect of the present invention, a fingerprint processing method includes a determining, based on a first degree, a plurality of feature points having a large value of the first degree among the feature points of a fingerprint specified in a fingerprint image of a matching source, the first degree representing a first distance to other feature points, as representative feature points used in matching processing of the fingerprint.

According to a third aspect of the present invention, a program causes a computer to execute a determining, based on a first degree, a plurality of feature points having a large value of the first degree among the feature points of a fingerprint specified in a fingerprint image of a matching source, the first degree representing a first distance to other feature points, as representative feature points used in match processing of the fingerprint.

According to a fourth aspect of the present invention, a fingerprint processing circuit includes a match processing circuit configured to determine, based on a first degree, a plurality of feature points having a large value of the first degree among the feature points of a fingerprint specified in a fingerprint image of a matching source, the first degree representing a first distance to other feature points, as representative feature points used in match processing of the fingerprint.

Advantageous Effects of Invention

According to the present invention, a fingerprint processing device, a fingerprint processing method, and a program capable of quickly performing matching without specifying the center of a fingerprint can be provided.

BRIEF DESCRIPTION OF THE DRAWINGS

FIG. 4 is a diagram showing the processing flow of the fingerprint processing device.

DESCRIPTION OF EMBODIMENTS

Hereunder, a fingerprint processing device according to an exemplary embodiment of the present invention will be described with reference to the drawings.

Figure 1:
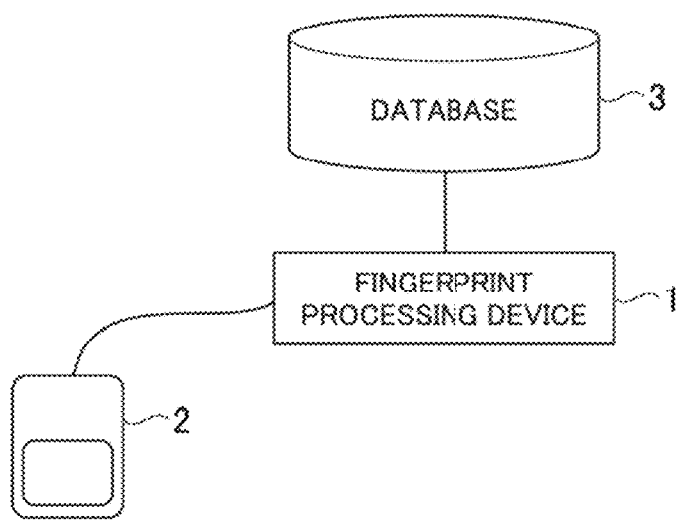
FIG. 1 is a diagram showing a fingerprint matching system including a fingerprint processing device.

FIG. 1 is a diagram showing a fingerprint matching system including a fingerprint processing device according to the same exemplary embodiment.

As shown in FIG. 1, the fingerprint matching system includes a fingerprint processing device 1, a fingerprint reader 2, and a database 3. The fingerprint processing device 1 is connected to the fingerprint reader 2 via a communication cable. Furthermore, the fingerprint processing device 1 is connected to the database 3 via a communication cable. The fingerprint processing device 1 performs fingerprint matching by comparing fingerprint information obtained from a fingerprint image acquired from the fingerprint reader 2 with fingerprint information stored in the database 3. The database 3 stores fingerprint information obtained from the fingerprint images of many people in advance.

Figure 2:
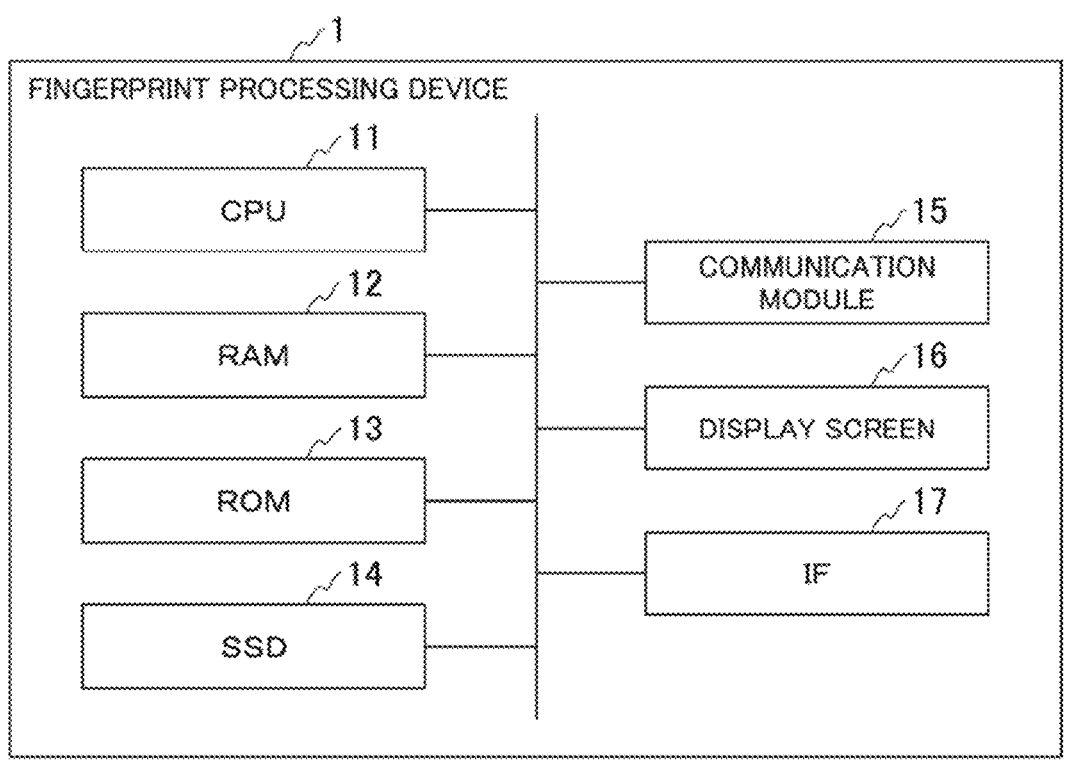
FIG. 2 is a hardware configuration diagram of the fingerprint processing device.

FIG. 2 is a hardware configuration diagram of the fingerprint processing device. The fingerprint processing device 1 may include; a CPU (Central Processing Unit) 11, a RAM (Random Access Memory) 12, a ROM (Read Only Memory) 13, an SSD (Solid State Drive) 14, a communication module 15, a display screen 16, and an IF (Interface) 17. The fingerprint processing device 1 is a computer provided with such functions.

Figure 3:
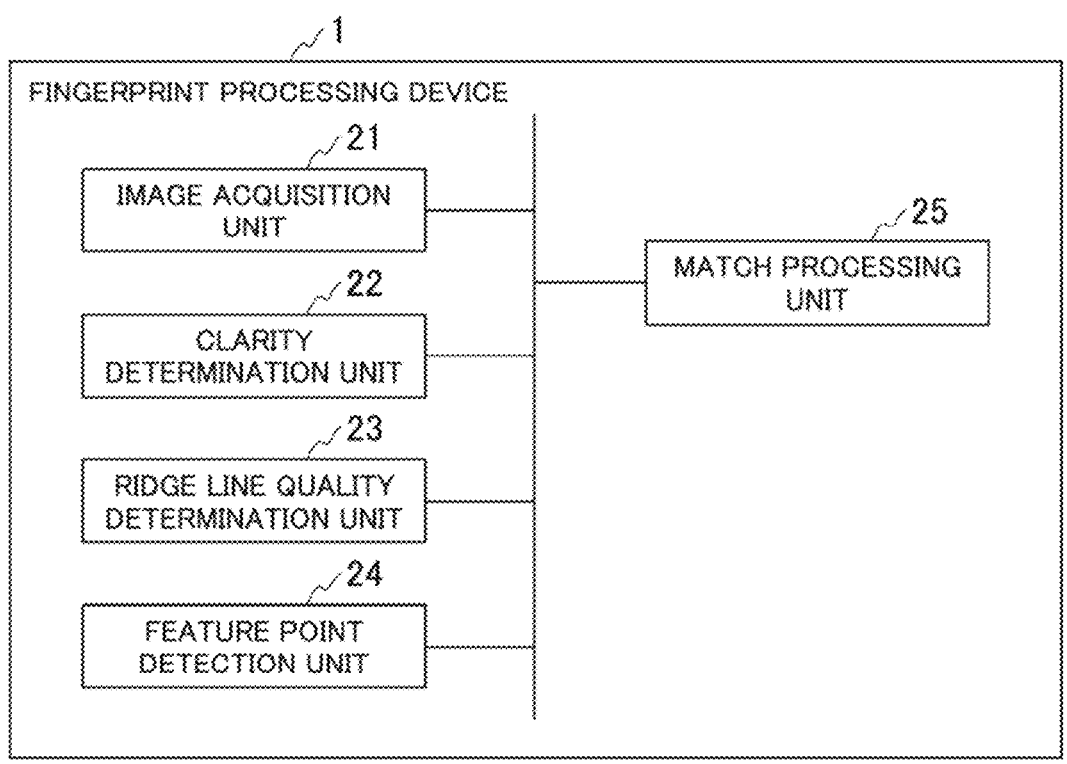
FIG. 3 is a functional block diagram of the fingerprint processing device.

FIG. 3 is a functional block diagram of the fingerprint processing device.

The fingerprint processing device 1 executes a fingerprint processing program in the CPU 11. Consequently, the fingerprint processing device 1 is provided with the functions of an image acquisition unit 21, a clarity determination unit 22, a ridge line quality determination unit 23, a feature point detection unit 24, and a match processing unit 25.

The image acquisition unit 21 acquires a fingerprint image from the fingerprint reader 2.

The clarity determination unit 22 determines and classifies the clarity of the fingerprint in each pixel of the fingerprint image.

The ridge line quality determination unit 23 determines the quality of the fingerprint ridge line appearing in each pixel in the fingerprint image.

The feature point detection unit 24 detects feature points of the fingerprint appearing in the fingerprint image.

The match processing unit 25 performs match processing by comparing the fingerprint information obtained from the fingerprint image acquired by the image acquisition unit 21, with the fingerprint information of a plurality of people recorded in the database 3.

In the present exemplary embodiment, the match processing unit 25 determines, based on a first degree, a plurality of feature points having a large value of the first degree among the feature points of a fingerprint specified in a fingerprint image of a matching source, the first degree representing that a distance to other feature points is large, as representative feature points used in fingerprint matching. That is to say, the match processing unit 25 acquires for each of the plurality of feature points of the fingerprint in the fingerprint image of the matching source, a first degree representing a first distance between the feature point and the other feature points. Then, the match processing unit 25 determines, among the plurality of feature points, a plurality of feature points having a large value of the first degree as representative feature points.

Alternatively, the match processing unit 25 determines, based on a second degree, a plurality of feature points having a large value of the second degree among the feature points of a fingerprint specified in a fingerprint image of a matching source, the second degree representing that a distance to a pixel region having an unknown image clarity specified in the fingerprint image is large, as representative feature points. That is to say, the match processing unit 25 acquires for each of the plurality of feature points of the fingerprint in the fingerprint image of the matching source, a second degree representing a second distance to a pixel region having an image clarity lower than a predetermined value. Then, the match processing unit 25 determines, among the plurality of feature points, a plurality of feature points having a large value of the second degree as representative feature points. The predetermined value is an arbitrary value for example.

Alternatively, the match processing unit 25 determines a plurality of representative feature points using a first degree, which represents that a distance to other feature points is large, and a second degree, which represents that a distance to a pixel region having an unknown (unclear) image clarity specified in the fingerprint image is large. For example, a representativeness may be calculated based on a value obtained by multiplying the first degree and the second degree, and the plurality of representative feature points may be determined based on the representativeness. That is to say, the match processing unit 25 calculates a representativeness based on a value obtained by multiplying the first degree and the second degree, and determines the plurality of feature points as representative feature points on the basis of the representativeness.

The match processing unit 25 may calculate the representativeness by further using the degree of stability of the ridge line in the pixels corresponding to the feature points of the fingerprint specified in the fingerprint image, and determine the representative feature points based on the representativeness.

Further, the match processing unit 25 specifies a plurality of representative feature points displaying a feature having a high representativeness, and performs match processing using the plurality of representative feature points in the fingerprint image of the matching source, and the plurality of representative feature points in the fingerprint image of a matching destination recorded in the database 3.

FIG. 4 is a diagram showing the processing flow of a fingerprint processing device.

Next, details of the processing of the fingerprint processing device 1 will be described step-by-step.

In the fingerprint processing device 1, the image acquisition unit 21 firstly acquires a fingerprint image from the fingerprint reader 2 (step S101). The image acquisition unit 21 temporarily records the fingerprint image in the RAM 12 or the like.

Then, the clarity determination unit 22 reads the fingerprint image from the RAM 12, and determines the clarity of each of the plurality of rectangular regions set throughout the entire fingerprint image (step S102). Each rectangular region may be a region that corresponds to a pixel, or may be a rectangular region set separately from a pixel. After determining the clarity of each rectangular region, the clarity determination unit 22 records an ID (identification) that specifies the rectangular region in the fingerprint image and the clarity of the rectangular region in the RAM 12. The clarity may be a binary value indicating clear or unclear for example. Any determination method of the clarity may be used. For example, the clarity determination unit 22 may calculate the clarity by processing equivalent to the processing performed by a quality index extraction means described in Japanese Unexamined Patent Application, First Publication No. Hei 10-177650.

Furthermore, the ridge line quality determination unit 23 reads the fingerprint image from the RAM 12, specifies the pixels in the rectangular region described above in the fingerprint image in which a ridge line appears, and determines the stability of the ridge line in the pixels thereof (step S103). The stability of a ridge line refers to the degree of stability of the width of a ridge line. The stability of a ridge line from the ridge line quality determination unit 23 is represented, for example, by variance values of both a black image that displays the finger print ridge line in the set rectangular region and a white image that displays regions between fingerprint ridge lines. The ridge line quality determination unit 23 determines rectangular regions, whose variance values for both the black image that displays the fingerprint ridge line and the white image that displays the regions between fingerprint ridge lines are higher than a threshold, represent rectangular regions that include ridge lines having a high stability. On the other hand, the ridge line quality determination unit 23 determines rectangular regions whose variance values for either the black image that displays the fingerprint ridge line or the white image that displays the interval between fingerprint ridge lines are less than or equal to a threshold, represent rectangular regions that include ridge lines having a low stability. The ridge line quality determination unit 23 records information that associates the ID of the rectangular region with a flag indicating whether the stability of the ridge line is high or low, in the RAM 12 or the like. A more detailed calculation of the stability of a ridge line may use, for example, the technique described as steps S301 to S305 in Japanese Patent (Granted) Publication No. 5,822,303.

The feature point detection unit 24 reads the fingerprint image from the RAM 12, and detects the feature points of the fingerprint appearing in the fingerprint image (step S104). A conventional detection method may be used for detecting the feature points. More specifically, the feature point detection unit 24 extracts two types of feature points from the fingerprint image.

Figure 5A:
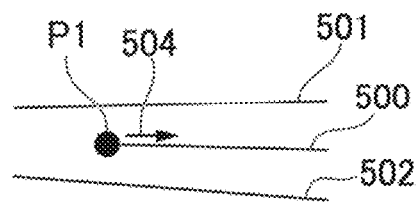
FIG. 5A is a diagram for describing a first feature point detected by a feature point detection unit.
Figure 5B:
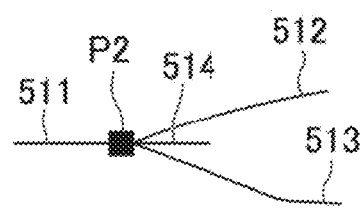
FIG. 5B is a diagram for describing a second feature point detected by the feature point detection unit.

FIG. 5A and FIG. 5B are diagrams for describing the feature points detected by the feature point detection unit.

A first feature point targeted by the feature point detection unit 24 is a terminal point (end point) of a ridge line. FIG. 5A illustrates a first feature point P1 sandwiched between two ridge lines 501 and 502. The feature point detection unit 24 detects the end point of a ridge line such as the first feature point P1 shown in FIG. 5A as a first feature point P1 of the input fingerprint image. Specifically, the feature point detection unit 24 detects first feature points P1 while scanning the entire fingerprint image.

A second feature point targeted by the feature point detection unit 24 is a branch point of a ridge line. FIG. 5B illustrates a second feature point P2 where a ridge line 511 branches into two ridge lines 512 and 513. The feature point detection unit 24 detects the branch point of a ridge line such as the second feature point P2 shown in FIG. 5B as a second feature point P2 of the input fingerprint image.

Next, the feature point detection unit 24 calculates an extension direction of the ridge line of the fingerprint extending from each detected feature point. As shown in FIG. 5A, for the first feature point P1, the direction in which the ridge line 500 emerges from the first feature point P1 (direction of arrow 504) is defined as the extension direction of the ridge line from the first feature point P1.

For the second feature point P2, this is illustrated in FIG. 5B. In a case where the ridge line 511 branches into the two ridge lines 512 and 513 at the second feature point P2, the direction proceeding between the two ridge lines (midpoint of the vectors) from the second feature point P2 (direction of arrow 514) is defined as the extension direction of the ridge line from the second feature point P2.

The feature point detection unit 24 records position information for the feature points detected in the fingerprint image and information about the extension direction of the ridge line extending from the feature points (extension direction information), in the RAM 12. The position information (coordinates) for the first feature points P1 and the second feature points P2 that were detected may be recorded in the form of a pixel position in the fingerprint image or as an ID of the rectangular region. Furthermore, the angle between the X axis and the extension direction of the ridge line from the feature point in an XY coordinate system having each feature point set as the origin may be recorded as the extension direction of the ridge line from each feature point.

Figure 6:
FIG. 6 is a diagram showing clear regions, unclear regions, and feature points determined in a fingerprint image.

FIG. 6 is a diagram showing clear regions, unclear regions, and feature points determined in a fingerprint image.

A shaded area displayed in the fingerprint image shown in the diagram indicates an unclear region E1 having a clarity that is less than a threshold value. Furthermore, an area which is not shaded indicates a clear region E2 having a clarity that is equal to or greater than the threshold value. In such a fingerprint image, local points in the image enclosed by circular symbols and square symbols represent feature points. Among the feature points, the feature points indicated by circular symbols represent first feature points P1. Among the feature points, the feature points indicated by square symbols represent second feature points P2. The straight lines emerging from the circular symbols and the square symbols indicate the extension direction of the ridge line extending from each feature point.

Figure 7:
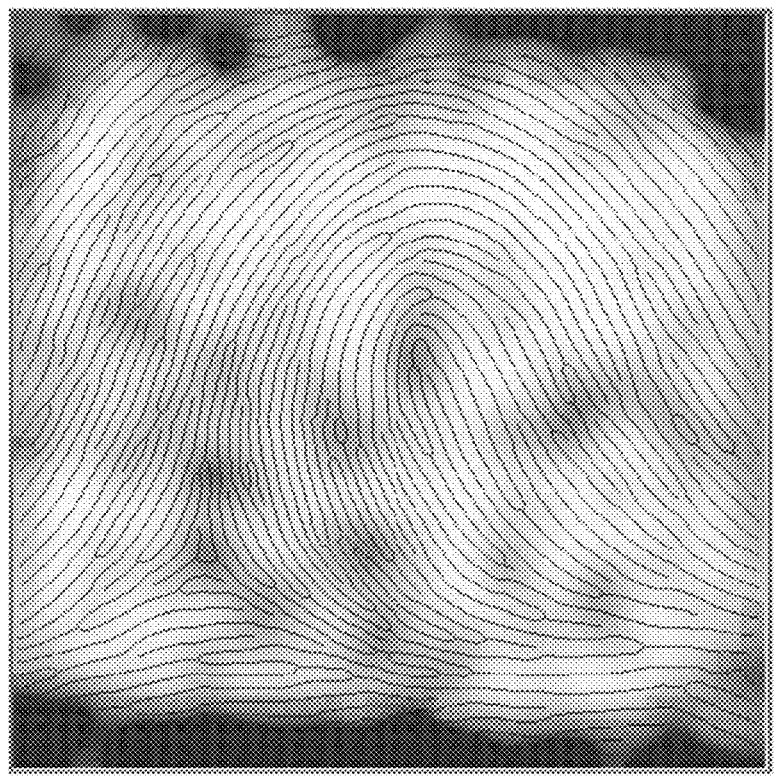
FIG. 7 is a diagram showing the stability of ridge lines determined in a fingerprint image.

FIG. 7 is a diagram showing the stability of ridge lines determined in a fingerprint image.

The fingerprint image shown in FIG. 7 displays a region in the clear region E2 indicated by a white section in which the stability (quality) of the ridge lines is high, and a region indicated by a black section in which the stability of the ridge lines is lower than a threshold. As a result of the processing in step S103, the fingerprint processing device 1 may output an image showing the distribution of the stability of the ridge lines shown in the manner of FIG. 7.

Returning to FIG. 4, the match processing unit 25 calculates a representativeness eval_p of each feature point using the position information and the extension direction information for each feature point detected by the feature point detection unit 24 (step S105). The representativeness is a frequency whose value becomes larger as the feature point specified in the fingerprint image becomes more separated from the other feature points. The representativeness eval_p may be a frequency indicating that, among the feature points specified in the fingerprint image, the distance from the other feature points is large and that the clarity is high.

Figure 8:
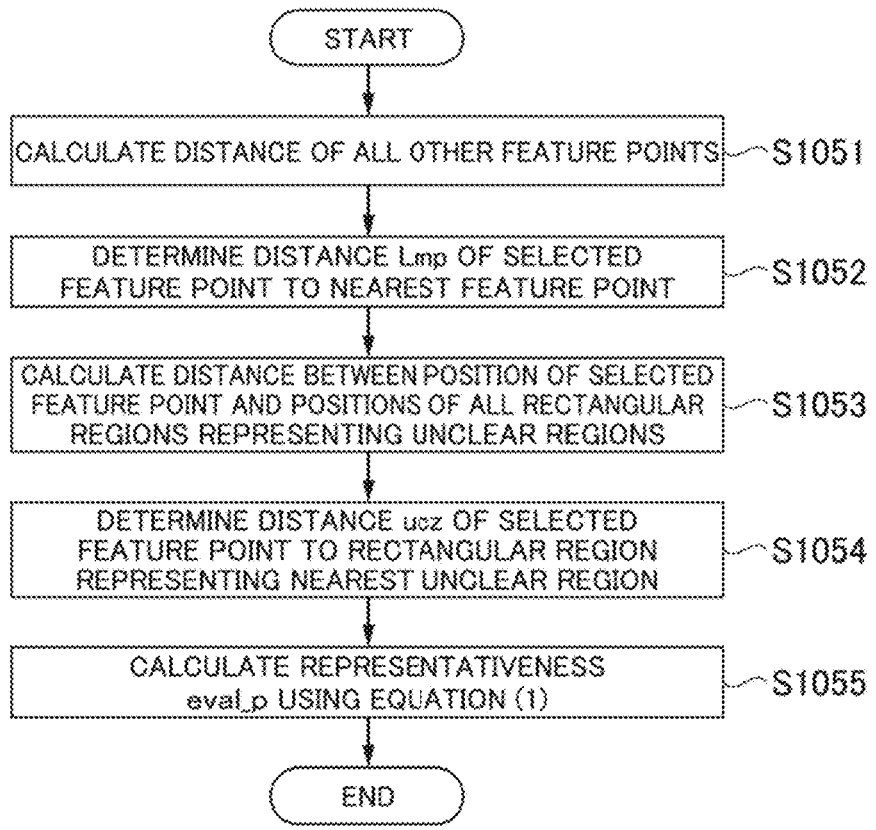
FIG. 8 is a diagram showing the processing flow of representativeness calculation processing.

FIG. 8 is a diagram showing the processing flow of representativeness calculation processing (step S105 in FIG. 4).

When calculating the representativeness eval_p, the match processing unit 25 firstly acquires the position information and the extension direction information for each feature point detected by the feature point detection unit 24, from the RAM 12. The match processing unit 25 selects one selected feature point from among the feature points and calculates the distance between the selected feature point thereof and all of the other feature points (step S1051). The match processing unit 25 determines the distance information having the smallest value among the plurality of calculated distances as a distance Lmp (first degree) to the nearest neighboring feature point from the selected feature point (step S1052).

Next, the match processing unit 25 calculates the respective distances between the selected feature point and each rectangular region using the position information of the selected feature point and the position information of all of the rectangular regions representing an unclear region E1 (step S1053). The match processing unit 25 determines the distance information having the smallest value among the calculated distances thereof as a distance ucz (min_ucz in equation (1)) (second degree) to the rectangular region representing the nearest neighboring unclear region E1 from the selected feature point (step S1054). Furthermore, the match processing unit 25 acquires information about the stability mRql of the ridge line in the pixels corresponding to the selected feature point, from the RAM 12. Then, the match processing unit 25 calculates the representativeness eval_p of the selected feature point according to equation (1) (step S1055).

$$eval\_p = (Lmp \times \min\_ucz)/A + mRql/B \quad \text{[Equation 1]}$$

In equation (1), A and B represent constants. Furthermore, "I" in equation (1) indicates division (÷). The constant A is a constant for performing an adjustment such that the value obtained by multiplying the distance Lmp to the nearest neighboring feature point from the selected feature point by the distance ucz to the rectangular region representing the nearest unclear region E1 from the selected feature point, does not become too large. The constant B is a constant for adjusting the value of the stability mRql of the ridge line of the pixels corresponding to the selected feature point. The representativeness eval_p, which represents a frequency indicating whether or not the distance of the selected feature point from the other feature points and the clarity are high, can be calculated according to equation (1). As a result of calculating the representativeness eval_p using the distance ucz to the rectangular region representing the nearest neighboring unclear region E1 from the selected feature point in the manner of equation (1), it is possible to calculate the representativeness eval_p while allowing for a case where other feature points exist in the unclear region E1.

In equation (1), information about the stability mRql of the ridge line in the pixels corresponding to the selected feature point is added. However, the representativeness eval_p may be calculated in a manner where the information is not added. Furthermore, in equation (1), information about the distance ucz to the rectangular region representing the nearest neighboring unclear region E1 to the selected feature point is added. However, the representativeness eval_p may be calculated in a manner where the information is not added.

Returning to FIG. 4, the match processing unit 25 determines whether or not calculation processing of the representativeness eval_p has been performed with respect to all of the feature points appearing in the fingerprint image as the selected feature point (step S106). The match processing unit 25 repeats the calculation of the representativeness eval_p until calculation processing of the representativeness eval_p is completed for all of the feature points appearing in the fingerprint image as the selected feature point. The match processing unit 25 searches the representativeness eval_p calculated for all of the feature points in descending order, and specifies a predetermined number of feature points having a large representativeness eval_p as representative feature points (step S107). The predetermined number may be a number such as 20 or 30 for example.

Figure 9:
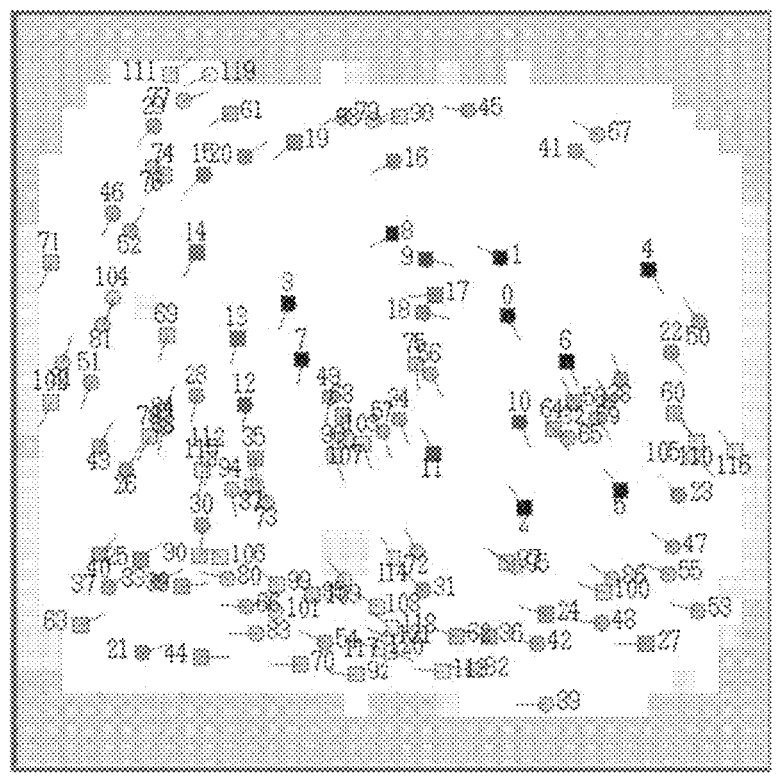
FIG. 9 is a diagram visually showing feature points and representative feature points.

FIG. 9 is a diagram visually showing feature points and representative feature points.

As shown in FIG. 9, many feature points are detected in a fingerprint image. The match processing unit 25 calculates the representativeness eval_p of each feature point and determines a predetermined number of feature points selected in descending order as representative feature points. In FIG. 9, the feature points where the symbol representing the feature point is displayed in black (dark) have a high (large) representativeness eval_p, and the feature points shown by the light color symbol have a low (small) representativeness eval_p.

Figure 10:
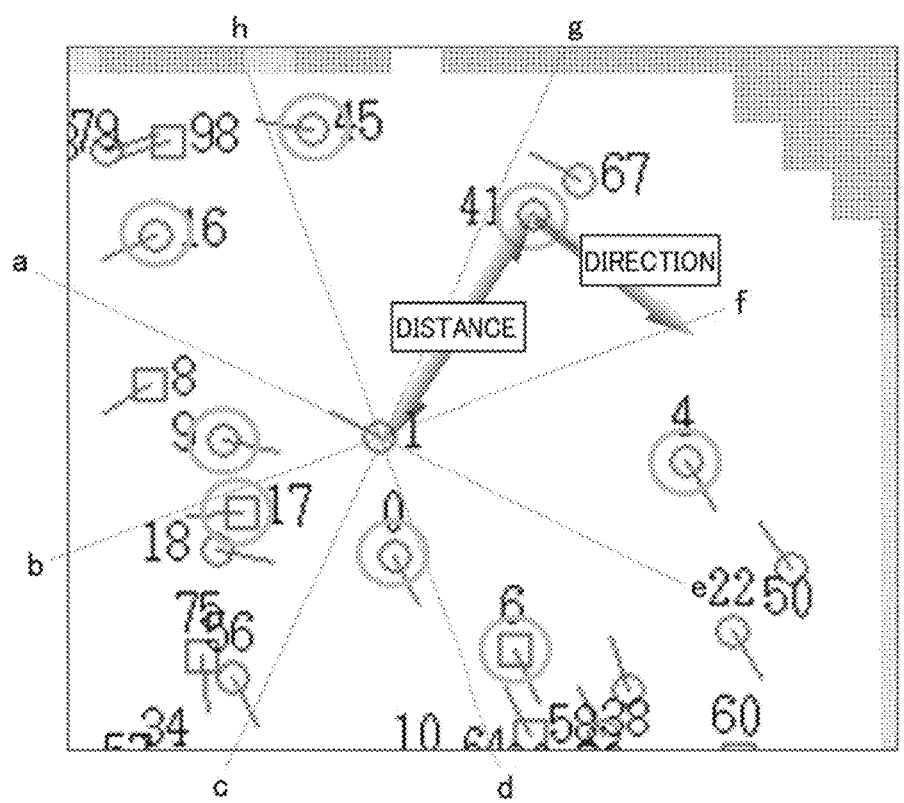
FIG. 10 is a first diagram showing an outline of feature amount specification processing of a representative feature point.

FIG. 10 is a first diagram showing an outline of feature amount specification processing of a representative feature point.

Figure 11:
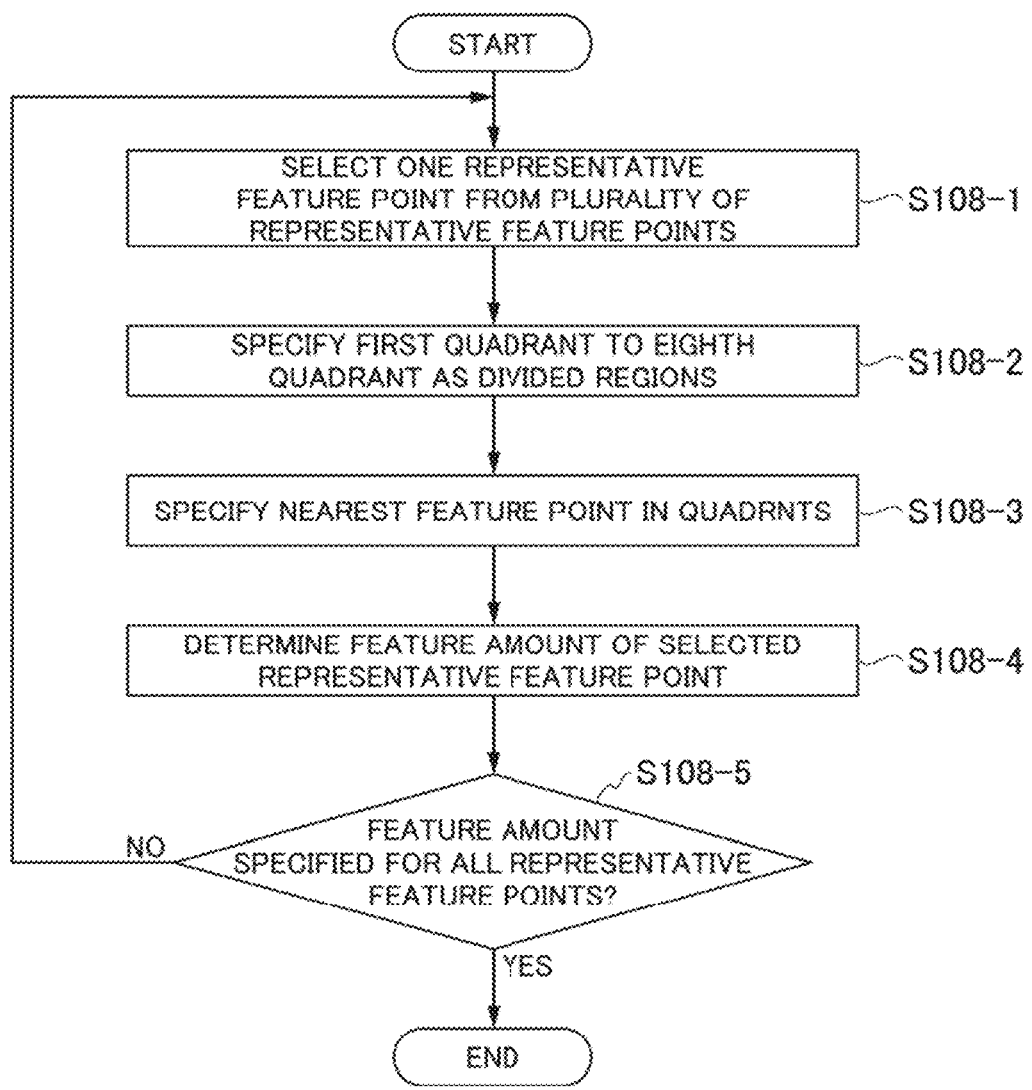
FIG. 11 is a first diagram showing the processing flow of processing that assigns a feature amount of a representative feature point.

FIG. 11 is a first diagram showing a processing flow of processing that assigns a feature amount of a representative feature point.

Next, the match processing unit 25 assigns a feature amount to each of the plurality of specified representative feature points (step S108 in FIG. 4). Here, the processing that assigns the feature amount in step S108 will be described according to the processing flow in FIG. 11.

Specifically, the match processing unit 25 selects one representative feature point from among the plurality of representative feature points (step S108-1). The selected representative feature point is referred to as a selected representative feature point. The match processing unit 25 reads the position information and the extension direction information (representative extension direction) for the selected representative feature point, from the RAM 12. Furthermore, the match processing unit 25 reads the position information and the extension direction information of the other feature points in the fingerprint image, from the RAM 12. The match processing unit 25 assumes that the extension direction indicated by the extension direction information (representative extension direction) for the selected representative feature point represents the positive direction of the vertical axis. Then, the match processing unit 25 specifies a first quadrant to an eighth quadrant as divided regions centered on the selected representative feature point and referenced to the vertical axis based on the extension direction information, such that the 360-degree direction on the fingerprint image plane is divided every 45 degrees (step S108-2).

Here, it is assumed that the match processing unit 25 has set the representative feature point assigned with the reference symbol 1 in FIG. 10 as the selected representative feature point. In this case, the axis in FIG. 10 having the selected representative feature point 1 as the origin and extending in the extension direction indicated by the extension direction information is referred to as axis a. The axis rotated about the selected representative feature point 1 to the left by 45 degrees from axis a is referred to as axis b. The axis rotated about the selected representative feature point 1 to the left by 45 degrees from axis b is referred to as axis c. The axis rotated about the selected representative feature point 1 to the left by 45 degrees from axis c is referred to as axis d. The axis rotated about the selected representative feature point 1 to the left by 45 degrees from axis d is referred to as axis e. The axis rotated about the selected representative feature point 1 to the left by 45 degrees from axis e is referred to as axis f. The axis rotated about the selected representative feature point 1 to the left by 45 degrees from axis f is referred to as axis g. The axis rotated about the selected representative feature point 1 to the left by 45 degrees from axis g is referred to as axis h.

The match processing unit 25 specifies the feature point 9 as having the shortest distance from the selected representative feature point 1 in the first quadrant between axis a and axis b (step S108-3). Furthermore, the match processing unit 25 specifies the feature point 17 as having the shortest distance from the selected representative feature point 1 in the second quadrant between axis b and axis c. Similarly, the match processing unit 25 specifies the feature points having the shortest distance to the selected representative feature point 1 in the third quadrant to the eighth quadrant divided by the axes. The match processing unit 25 determines the distance from the selected representative feature point 1 to each feature point specified in the first quadrant to the eighth quadrant, the extension direction information for each feature point specified in the first quadrant to the eighth quadrant, and the representativeness calculated for the selected representative feature point 1 collectively as the feature amount of the selected representative feature point 1 (step S108-4). The match processing unit 25 determines whether or not a feature amount has been specified for all of the representative feature points (step S108-5). If the match processing unit 25 has not specified a feature amount for all of the representative feature points (NO in step S108-5), it repeats the processing that specifies the feature amount.

When the match processing unit 25 has specified the feature amount for all of the representative feature points (YES in step S108-5), then returning to FIG. 4, information that includes the feature amount for all of the representative feature points is determined as the fingerprint feature amount for the fingerprint image acquired from the fingerprint reader 2 (step S109). The fingerprint image obtained from fingerprint reader 2 is referred to as the authentication fingerprint image below. The match processing unit 25 reads the fingerprint feature amount of the first fingerprint image recorded in the database 3. The fingerprint image recorded in the database 3 is referred to as the search destination fingerprint image below. The fingerprint feature amount of the search destination fingerprint image is a feature amount calculated in the same manner as the calculation of the fingerprint feature amount of the authentication fingerprint image. The match processing unit 25 calculates a degree of similarity using the fingerprint feature amount of the authentication fingerprint image and the fingerprint feature amount of the search destination fingerprint image (step S110). The calculation of the degree of similarity is an aspect of the match processing.

Figure 12:
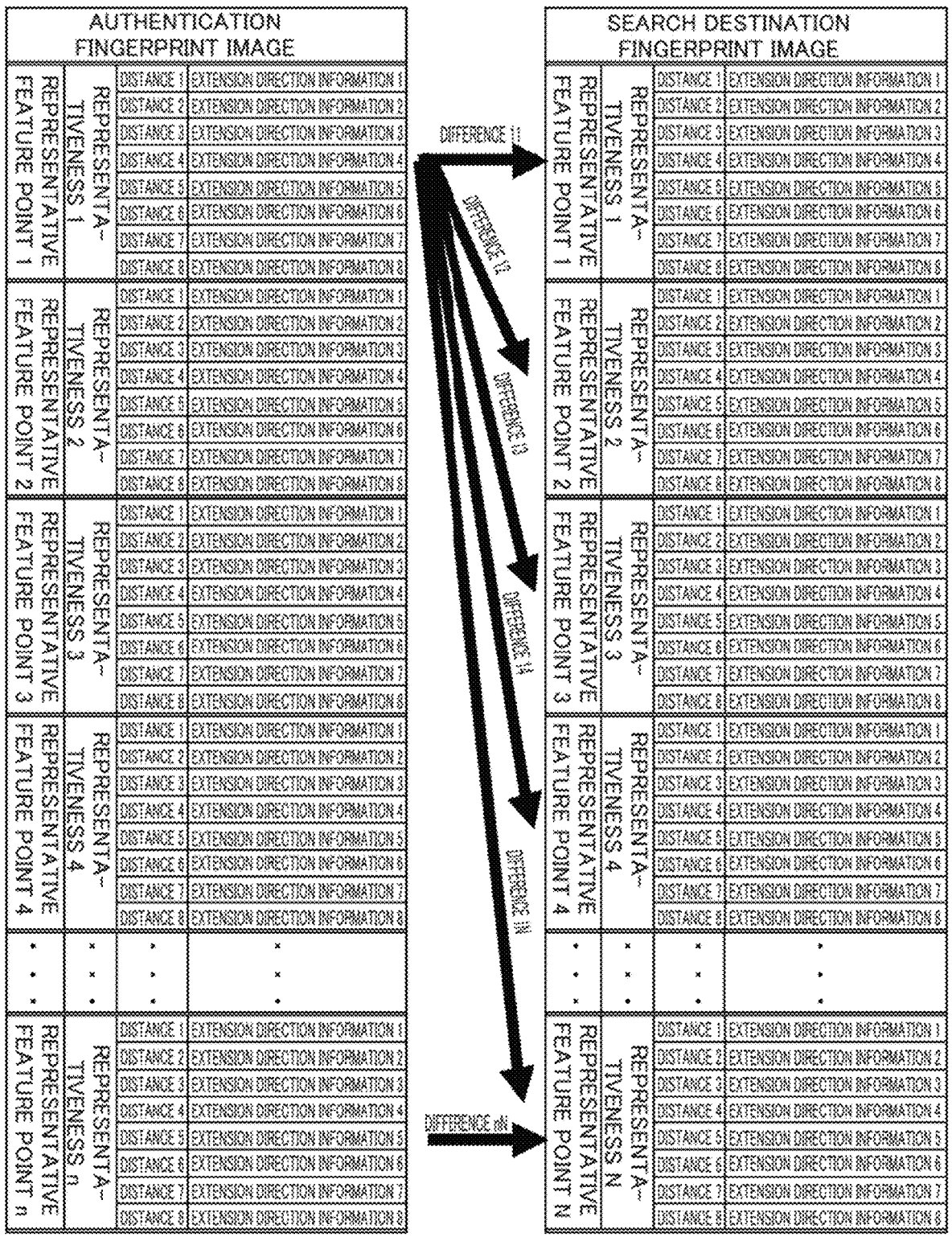
FIG. 12 is a first diagram showing an outline of degree of similarity calculation processing based on a fingerprint feature amount.

FIG. 12 is a first diagram showing an outline of degree of similarity calculation processing based on a fingerprint feature amount.

As shown in FIG. 12, for each of the plurality of representative feature points specified in the authentication fingerprint image, the match processing unit 25 records fingerprint feature amount information that includes; the representativeness, the distance to the nearest neighboring feature points specified in the first quadrant to the eighth quadrant, and extension direction information representing the extension direction of the ridge line extending from the nearest neighboring feature points, in the RAM 12. The plurality of search destination fingerprint images recorded in the database 3 is composed of the same fingerprint feature amount information.

The match processing unit 25 calculates by brute force, the difference between each representative feature point on the authentication fingerprint image side and each representative feature point in the search destination fingerprint image. When the difference between one representative feature point on the authentication fingerprint image side and one representative feature point in the search destination fingerprint image is calculated, a value in which the difference in the distance to the nearest neighboring feature point, and the difference in the direction represented by the extension direction information, are each multiplied by the representativeness on the authentication fingerprint image side and then added together is calculated for corresponding and equivalent quadrants, and then a cumulative value for the values thereof is obtained for the eight quadrants. The cumulative value represents the difference between one representative feature point in the authentication fingerprint image and one representative feature point in the search destination fingerprint image.

The representative feature points specified in the authentication fingerprint image are denoted as 1 to n, and the representative feature points specified in the search destination fingerprint image are denoted as 1 to N. The match processing unit 25 calculates the respective differences between one representative feature point in the authentication fingerprint image and each representative feature point in the search destination fingerprint image.

If the one representative feature point in the authentication fingerprint image is denoted as the representative feature point 1, the match processing unit 25 calculates the differences S (11, 12, . . . , 1N) between the representative feature point 1 in the authentication fingerprint image thereof and each representative feature point 1 to N in the search destination fingerprint image.

The match processing unit 25 specifies the representative feature point in the search destination fingerprint image having the smallest difference S among the calculated differences S. As a result of the processing, the match processing unit 25 is able to specify the representative feature points included in the search fingerprint image that are near the one representative feature point 1 specified in the authentication fingerprint image.

The match processing unit 25 specifies the representative feature point in the search destination fingerprint image having a small difference S for all of the representative feature points (1 to n) in the authentication fingerprint image.

The match processing unit 25 sorts the differences S between the representative feature points in the search destination fingerprint image specified for each representative feature point (1 to n) in the authentication fingerprint image in ascending order, and calculates an average value of a fixed number (2 to 4) of values in ascending order. The match processing unit 25 calculates the degree of similarity between the authentication fingerprint image and the search destination fingerprint image by subtracting the average value thereof from a constant. The value of a search fingerprint image having a high degree of similarity is such that a small value is subtracted from the constant. Therefore, the value of the degree of similarity becomes high.

Returning to FIG. 4, the match processing unit 25 calculates a degree of similarity with respect to the authentication fingerprint image using all of the search destination fingerprint images included in the database 3. The match processing unit 25 determines the search destination fingerprint images having a degree of similarity higher than a reference threshold as match candidates, which are subjected to a more detailed match determination with respect to the authentication fingerprint image (step S111). The match processing unit 25 performs matching between the authentication fingerprint image and the search destination fingerprint images determined as match candidates by using the feature points included in each fingerprint image (step S112). A known technique that performs match determination using feature points may be used for the match processing. As a result of match determination, the match processing unit 25 determines and outputs the search destination fingerprint image having the highest degree of similarity among the search destination fingerprint images having a degree of similarity higher than a reference value, as the fingerprint image matching the authentication fingerprint image (step S113). As a result of match determination, if the match processing unit 25 is unable to find a search destination fingerprint image having a high degree of similarity, it outputs information indicating that no match was found (step S114).

The processing mentioned above will be described briefly. Firstly, the match processing unit 25 specifies for one extracted representative feature point extracted from the plurality of representative feature points a representative extension direction of the ridge line of the fingerprint extending from the extracted representative feature point. Furthermore, the match processing unit 25 assigns a feature amount, which is determined based on; the distance to the neighboring feature point determined based on the extracted representative feature point, the extension direction of the ridge line of the fingerprint extending from the neighboring feature point referenced to the representative extension direction, and the representativeness of the neighboring feature point, to the extracted representative feature point.

That is to say, the match processing unit 25 assigns a feature amount, which is determined based on; the distance to the neighboring feature point of the representative feature point, the extension direction of the ridge line of the neighboring feature point, and the representativeness of the neighboring feature point, to each representative feature point. The neighboring feature point of the representative feature point is a feature point that neighbors the representative feature point in each of eight quadrant regions, which are referenced to the representative extension direction of the representative feature point and have the representative feature point as the origin.

Then, the match processing unit 25 uses the feature amounts, which are similarly assigned to each of the extracted representative feature points, to perform match processing of the fingerprint using the plurality of representative feature points in the fingerprint image of the matching source (authentication fingerprint image) and the plurality of representative feature points in the fingerprint image of the matching destination (search destination fingerprint image).

Figure 13:
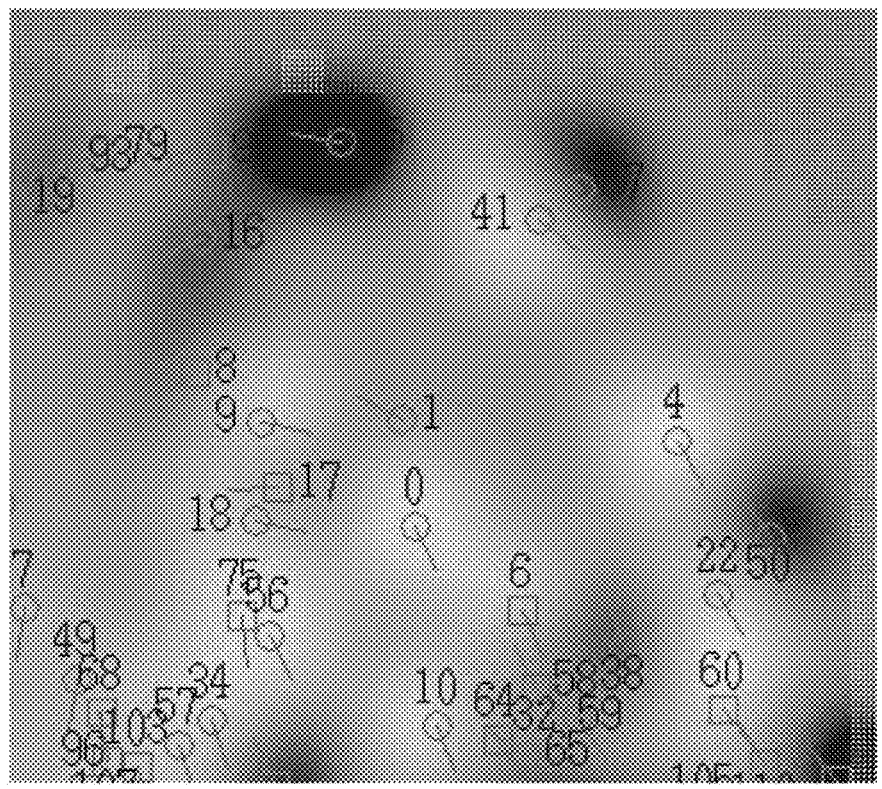
FIG. 13 is a second diagram showing an outline of feature amount specification processing of a representative feature point.

FIG. 13 is a second diagram showing an outline of feature amount specification processing of a representative feature point.

Figure 14:
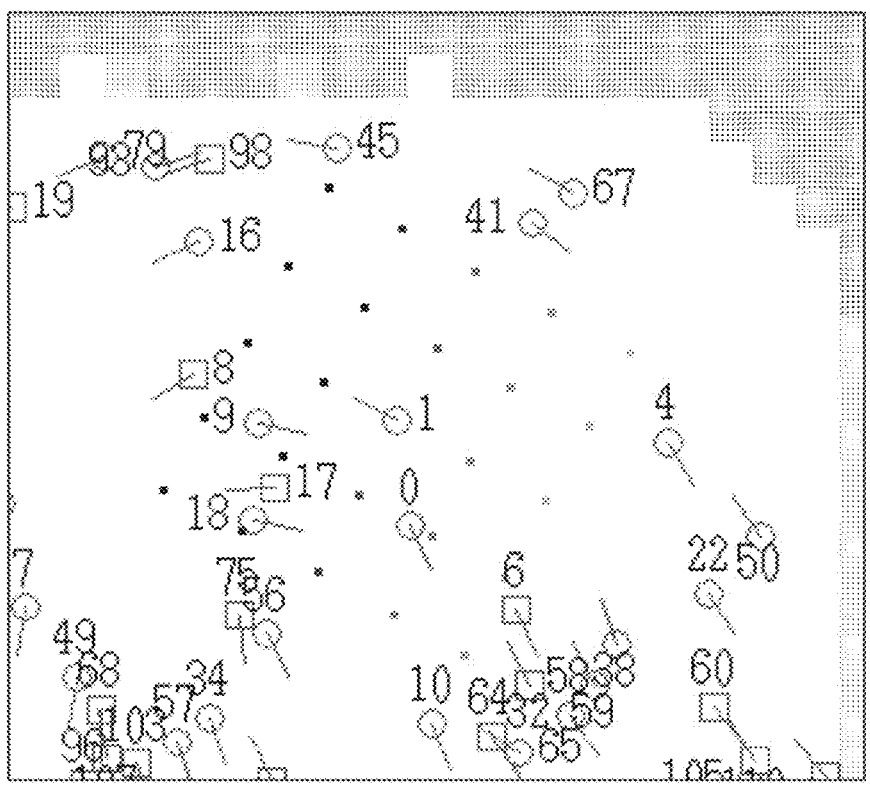
FIG. 14 is a third diagram showing an outline of feature amount specification processing of a representative feature point.

FIG. 14 is a third diagram showing an outline of feature amount specification processing of a representative feature point.

Figure 15:
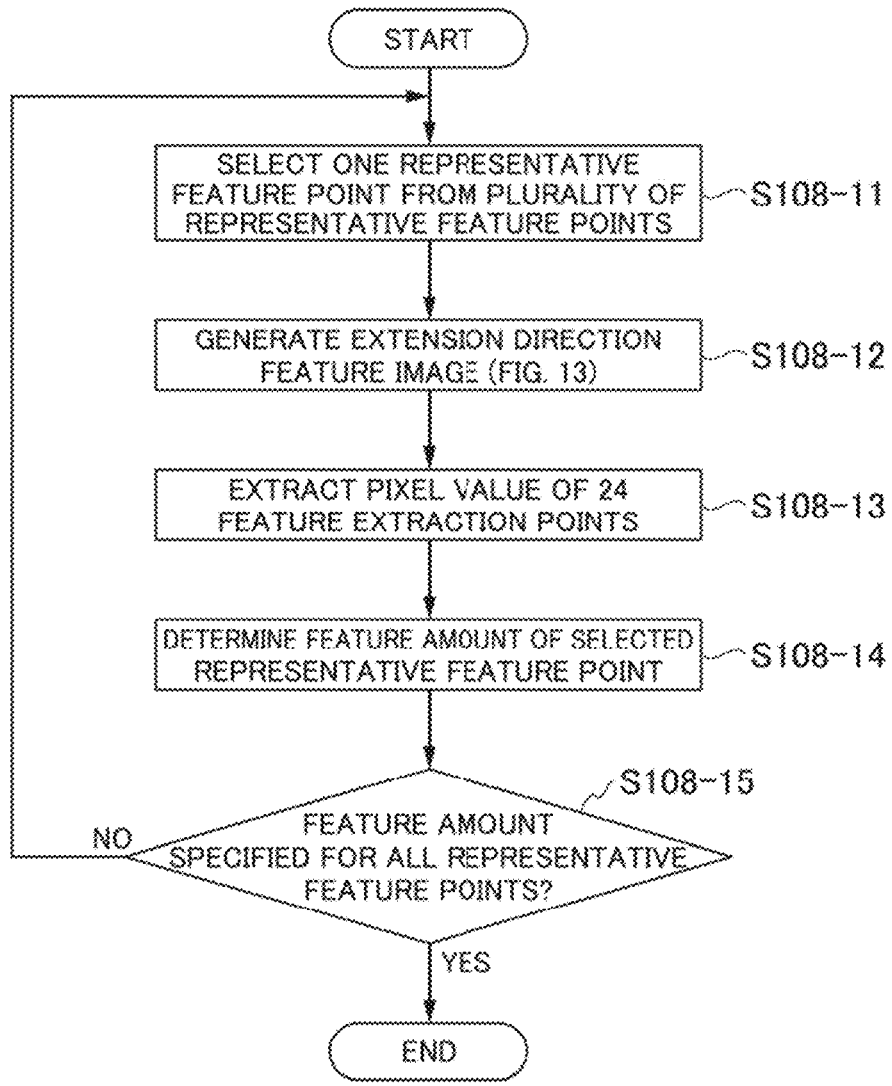
FIG. 15 is a second diagram showing the processing flow of processing that assigns a feature amount of a representative feature point.

FIG. 15 is a second diagram showing the processing flow of processing that assigns a feature amount of a representative feature point.

The match processing unit 25 may specify the match candidate search destination fingerprint images using a method other than the processing described using FIG. 10 to FIG. 12.

The match processing unit 25 assigns a feature amount to each of the plurality of specified representative feature points (step S108 in FIG. 4). Another example of the processing that assigns the feature amount in step S108 will be described according to the processing flow of FIG. 15.

Specifically, the match processing unit 25 selects one representative feature point from among the plurality of representative feature points (step S108-11). In FIG. 13, the representative feature point indicated by the reference symbol 1 is the selected representative feature point. The selected representative feature point is referred to as a selected representative feature point. The match processing unit 25 reads the position information and the extension direction information for the selected representative feature point from the RAM 12. The match processing unit 25 reads the position information and the extension direction information of the other feature points in the fingerprint image (which include feature points other than the representative feature points) from the RAM 12. The match processing unit 25 assumes that the extension direction indicated by the extension direction information for the selected representative feature point represents the positive direction of the vertical axis. Further, the match processing unit 25 generates a ridge line extension direction determination image (FIG. 13), in which the other feature points whose extension direction is in the opposite direction to the extension direction of the vertical axis have the pixels neighboring the feature point colored in white, and the other feature points whose extension direction is in the same direction as the extension direction of the vertical axis have the pixels neighboring the feature point colored in black (step S108-12). For part of the ridge line extension direction determination image not specified as a black color or a white color, an interpolated color value may be calculated based on the colors (pixel values) of other neighboring pixels, such that it has a pixel value of any gradation among the gradation values from a black to white color. Consequently, in FIG. 13, it can be understood that for the feature point 50, whose extension direction is in the same direction as the extension direction of the ridge line of the selected representative feature point 1, the surrounding pixels thereof have a black color. Furthermore, in FIG. 13, it can be understood that for the feature point 9 and the feature point 6, whose extension directions are in the opposite direction to the extension direction of the ridge line of the selected representative feature point 1, the surrounding pixels thereof have a white color.

The match processing unit 25 extracts for the ridge line extension direction determination image generated for the selected representative feature point 1 (FIG. 13), the pixel values of 24 feature extraction points (24 points) centered on the position of the selected representative feature point 1 (step S108-13). FIG. 14 illustrates the positions of the 24 feature extraction points (1) to (24) centered on the position of the selected representative feature point 1. The match processing unit 25 determines information that represents a listing of pixel values for the feature extraction points (1) to (24), and the stability of the ridge line calculated for the representative feature points as the fingerprint feature amount of the selected representative feature point 1 (step S108-14). The match processing unit 25 determines whether or not a fingerprint feature amount has been calculated for all of the representative feature points (step S108-15). If a fingerprint feature amount has not been calculated for all of the representative feature points (NO in step S108-15), the match processing unit 25 generates a fingerprint feature amount for the other representative feature points using the same method.

When the match processing unit 25 has calculated a fingerprint feature amount for all of the representative feature points specified in the authentication fingerprint image (YES in step S108-5), then returning to FIG. 4, information that includes the fingerprint feature amount for all of the representative feature points is determined as the fingerprint feature amount for the authentication fingerprint image (step S109). The fingerprint feature amount of the search destination fingerprint image is a feature amount calculated in the same manner as the calculation of the fingerprint feature amount of the authentication fingerprint image. The relationship between the representative feature point and the positions of the feature extraction points (1) to (24) in the authentication fingerprint image is the same as the relationship between the position of the representative feature point and the positions of the feature extraction points (1) to (24) in the search destination fingerprint image. The match processing unit 25 calculates a degree of similarity using the fingerprint feature amount of the authentication fingerprint image and the fingerprint feature amount of the search destination fingerprint image (step S110).

Figure 16:
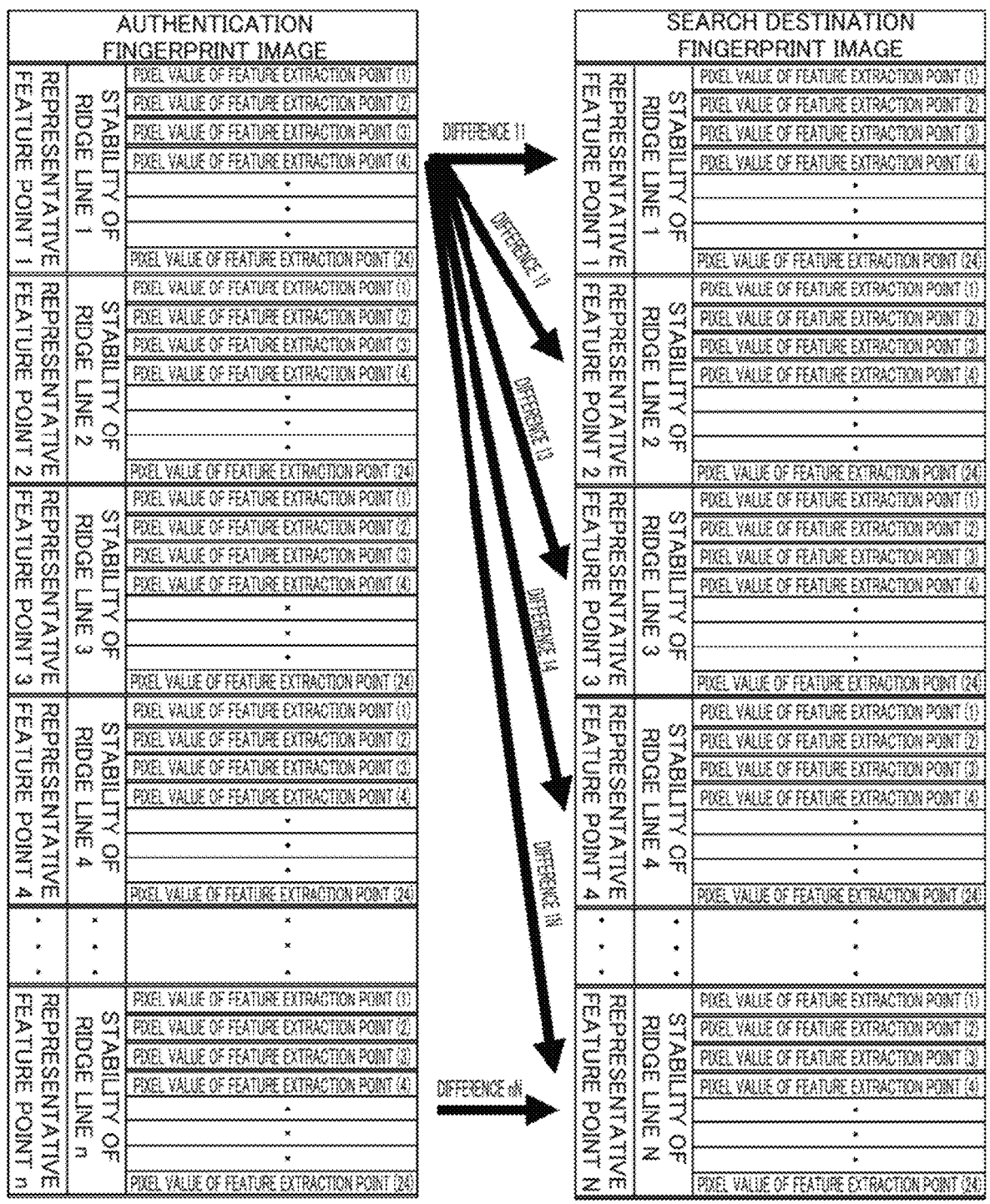
FIG. 16 is a second diagram showing an outline of degree of similarity calculation processing based on a fingerprint feature amount.

FIG. 16 is a second diagram showing an outline of degree of similarity calculation processing based on a fingerprint feature amount.

As shown in the diagram, the fingerprint feature amount of the authentication fingerprint image includes; the stability of the ridge line (ridge line quality) in the pixels (or rectangular regions) corresponding to the plurality of representative feature points specified from among many feature points, and the pixel values of the surrounding feature extraction points (1) to (24) referenced to the representative feature point thereof. The plurality of search destination fingerprint images recorded in the database 3 is composed of the same fingerprint feature amount information.

The match processing unit 25 calculates by brute force, the difference between each representative feature point on the authentication fingerprint image side and each representative feature point in the search destination fingerprint image. When the difference S between one representative feature point on the authentication fingerprint image side and one representative feature point in the search destination fingerprint image is calculated, a value in which the difference in the pixel value of the corresponding feature extraction point is multiplied by the stability of the ridge line of the authentication fingerprint image is calculated and accumulated for each of the 24 feature extraction points. The cumulative value represents the difference S between one representative feature point in the authentication fingerprint image and one representative feature point in the search destination fingerprint image.

The representative feature points specified in the authentication fingerprint image are denoted as 1 to n, and the representative feature points specified in the search destination fingerprint image are denoted as 1 to N. The match processing unit 25 calculates the respective differences S between one representative feature point in the authentication fingerprint image and each representative feature point in the search destination fingerprint image.

If one representative feature point in the authentication fingerprint image is denoted as the representative feature point 1, the match processing unit 25 calculates the differences S (11, 12, . . . , 1N) between the representative feature point 1 in the authentication fingerprint image thereof and each representative feature point 1 to N in the search destination fingerprint image.

The match processing unit 25 specifies the representative feature point in the search destination fingerprint image having the smallest difference S among the calculated differences S. As a result of the processing, the match processing unit 25 is able to specify the representative feature points included in the search fingerprint image that are near the one representative feature point 1 specified in the authentication fingerprint image.

The match processing unit 25 specifies the representative feature point in the search destination fingerprint image having a small difference S for all of the representative feature points (1 to n) in the authentication fingerprint image.

The match processing unit 25 sorts the differences S between the representative feature points in the search destination fingerprint image specified for each representative feature point (1 to n) in the authentication fingerprint image in ascending order, and calculates an average value of a fixed number (2 to 4) of values in ascending order. The match processing unit 25 calculates the degree of similarity between the authentication fingerprint image and the search destination fingerprint image by subtracting the average value thereof from a constant. Since the value of a search fingerprint image having a high degree of similarity is such that a small value is subtracted from the constant, the value of the degree of similarity becomes high.

Returning to FIG. 4, the match processing unit 25 calculates a degree of similarity with respect to the authentication fingerprint image using all of the search destination fingerprint images included in the database 3. The match processing unit 25 determines the search destination fingerprint image having a degree of similarity higher than a reference threshold as match candidates, which are subjected to a more detailed match determination with respect to the authentication fingerprint image (step S111). The match processing unit 25 performs matching between the authentication fingerprint image and the search destination fingerprint images determined as match candidates by using the feature points included in each fingerprint image. A known technique that performs match determination using feature points may be used for the match processing. As a result of match determination, the match processing unit 25 determines the search destination fingerprint image having the highest degree of similarity as the fingerprint image matching the authentication fingerprint image (step S112). As a result of match determination, if the match processing unit 25 is unable to find a search destination fingerprint image having a high degree of similarity, it outputs information indicating that no match was found (step S113).

The processing mentioned above will be briefly described. Firstly, the match processing unit 25 specifies for one extracted representative feature point extracted from the plurality of representative feature points, a representative extension direction of the ridge line of the fingerprint extending from the extracted representative feature point. Then, the match processing unit 25 generates a ridge line extension direction determination image that represents; pixel values of neighboring feature points indicating that the degree of matching of the extension direction referenced to the representative extension direction of the ridge line of the fingerprint extending from the neighboring feature point determined based on the extracted representative feature point, with respect to the representative extension direction is high, and pixel values of neighboring feature points indicating that the degree of matching with respect to the representative extension direction is low.

That is to say, the match processing unit 25 specifies the extension direction of the ridge line of the neighboring feature points, which are determined based on the representative feature point. Furthermore, the match processing unit 25 generates a ridge line extension direction determination image that includes pixel values of the neighboring feature points indicating that the degree of matching between the specified extension direction and the representative extension direction is high, and pixel values of the neighboring feature points indicating that the degree of matching between the specified extension direction and the representative extension direction is low. Then, the match processing unit 25 assigns a feature amount representing a plurality of pixel values at predetermined positions referenced to the position of the representative feature point in the ridge line extension direction determination image, to the representative feature point.

Further, the match processing unit 25 assigns the feature amount representing the plurality of pixel values at predetermined positions referenced to the position of the corresponding extracted representative feature point in the ridge line extension direction determination image, to the representative feature point. The match processing unit 25 uses the feature amounts, which are similarly assigned to each of the extracted representative feature points, to perform match processing of the fingerprint using the plurality of representative feature points in the fingerprint image of the matching source and the plurality of representative feature points in the fingerprint image of the matching destination.

Although the foregoing has described an exemplary embodiment of the present invention, according to the processing mentioned above, because the match processing is performed without specifying the center of a fingerprint, the match processing can be performed without requiring specification accuracy with respect to the center of the fingerprint.

Furthermore, simple arithmetic operations and sort processing are used in the processing mentioned above that determines the search destination fingerprint image of a match candidate. Moreover, the feature points used in the calculations are limited to a small number of feature points such as representative feature points and feature extraction points. Consequently, the processing required to determine a match candidate can be reduced.

In addition, in the match processing, because the match processing of an authentication fingerprint image is performed using a search destination fingerprint image specified as a match candidate, the processing can be reduced.

In the above description, the fingerprint processing device 1 was described assuming that it performs either the degree of similarity calculation described using FIG. 10 to FIG. 12 or the degree of similarity calculation described using FIG. 13 to FIG. 16. However, both degree of similarity calculations may be performed to specify a match candidate in which the degree of similarity is high for each calculation.

Figure 17:
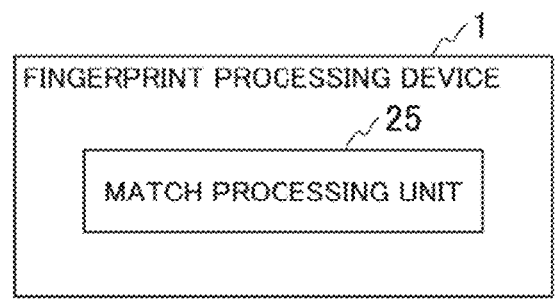
FIG. 17 is a diagram showing a minimum configuration of the fingerprint processing device.

FIG. 17 is a diagram showing a minimum configuration of the fingerprint processing device.

As shown in the diagram, the fingerprint processing device 1 includes at least the match processing unit 25 that determines, based on a first degree, a plurality of feature points having a large value of the first degree among the feature points of a fingerprint specified in a fingerprint image of a matching source, the first degree representing that the distance to other feature points is large, as representative feature points used in fingerprint matching.

The fingerprint processing device 1 according to the present exemplary embodiment may be defined as a match processing circuit having at least the functions of the match processing unit 25 described above.

The fingerprint processing device 1 mentioned above has an internal computer system. Further, a program for causing the fingerprint processing device 1 to perform the processing mentioned above is stored on a computer-readable recording medium of the fingerprint processing device 1, and the processing described above is performed by the computer of the fingerprint processing device 1 reading and executing the program. Here, the computer-readable recording medium refers to a magnetic disk, a magneto-optical disk, a CD-ROM, a DVD-ROM, a semiconductor memory, or the like. Furthermore, the computer program may be transmitted to the computer by means of a communication line, and the computer receiving the transmission may execute the program.

Moreover, the program described above may be one that realizes a portion of the functions of the processing units mentioned above. Further, the program may be one that realizes the functions mentioned above by being combined with a program already recorded on the computer system, as a so-called difference file (difference program).

The exemplary embodiments described above may also be described entirely or in part by the following supplementary notes, without being limited to the following.

(Supplementary Note 1)

A fingerprint processing device including a match processing unit configured to determine, based on a first degree, a plurality of feature points having a large value of the first degree among the feature points of a fingerprint specified in a fingerprint image of a matching source, the first degree representing a first distance to other feature points, as representative feature points used in match processing of the fingerprint.

(Supplementary Note 2)

The fingerprint processing device according to Supplementary Note 1, wherein the match processing unit is configured to determine, further based on a second degree, a plurality of feature points having a large value of the second degree among the feature points, the second degree representing a second distance to a pixel region specified in the fingerprint image having an image clarity lower than a predetermined value, as the representative feature points.

(Supplementary Note 3)

The fingerprint processing device according to Supplementary Note 2, wherein the match processing unit is configured to calculate a representativeness based on a value obtained by multiplying the first degree and the second degree, and the representative feature points are determined further based on the representativeness.

(Supplementary Note 4)

The fingerprint processing device according to Supplementary Note 3, wherein the match processing unit is configured to calculate the representativeness by further using a degree of stability of the ridge line in the pixels that correspond to the feature points, and determine the representative feature points based on the representativeness.

(Supplementary Note 5)

The fingerprint processing device according to Supplementary Note 3 or Supplementary Note 4, wherein the match processing unit is configured to determine a plurality of representative feature points having a high representativeness, and perform the match processing using the plurality of representative feature points in a fingerprint image of the matching source and a plurality of representative feature points in a fingerprint image of a matching destination.

(Supplementary Note 6)

The fingerprint processing device according to Supplementary Note 5, wherein the match processing unit is configured to specify, for each of the plurality of representative feature points, a representative extension direction of a ridge line extending from the representative feature point, and assign a feature amount determined based on a distance to a neighboring feature point determined based on the representative feature point, an extension direction of a ridge line extending from the neighboring feature point, and the representativeness of the neighboring feature point; and perform the match processing of the fingerprint using the feature amount assigned to each of the representative feature points, and based on the plurality of representative feature points in a fingerprint image of the matching source and the plurality of representative feature points in a fingerprint image of the matching destination.

(Supplementary Note 7)

The fingerprint processing device according to Supplementary Note 6, wherein the neighboring feature point determined based on the representative feature point is a feature point neighboring the representative feature point in each of eight quadrant regions referenced to the representative extension direction of the representative feature point and having the representative feature point as an origin.

(Supplementary Note 8)

The fingerprint processing device according to Supplementary Note 5, wherein the match processing unit is configured to specify, for each of the plurality of representative feature points, a representative extension direction of a ridge line extending from the representative feature point, generate a ridge line extension direction determination image that includes a pixel value of a neighboring feature point indicating that a degree of matching between an extension direction of a ridge line extending from the neighboring feature point determined based on the representative feature point and the representative extension direction is high, and a pixel value of the neighboring feature point indicating that a degree of matching between the extension direction of the ridge line extending from the neighboring feature point and the representative extension direction is low, and assigns a feature amount representing a plurality of pixel values at predetermined positions referenced to the position of the representative feature point in the ridge line extension direction determination image; and perform the match processing of the fingerprint using the feature amount assigned to each of the representative feature points, and based on the plurality of representative feature points in a fingerprint image of the matching source and the plurality of representative feature points in a fingerprint image of the matching destination.

(Supplementary Note 9)

A fingerprint processing method including a determining, based on a first degree, a plurality of feature points having a large value of the first degree among the feature points of a fingerprint specified in a fingerprint image of a matching source, the first degree representing a first distance to other feature points, as representative feature points used in match processing of the fingerprint.

(Supplementary Note 10)

A program that causes a computer to execute a determining, based on a first degree, a plurality of feature points having a large value of the first degree among the feature points of a fingerprint specified in a fingerprint image of a matching source, the first degree representing a first distance to other feature points, as representative feature points used in match processing of the fingerprint.

(Supplementary Note 11)

A fingerprint processing circuit including a match processing circuit configured to determine, based on a first degree, a plurality of feature points having a large value of the first degree among the feature points of a fingerprint specified in a fingerprint image of a matching source, the first degree representing a first distance to other feature points, as representative feature points used in match processing of the fingerprint.

INDUSTRIAL APPLICABILITY

According to the present invention, a fingerprint processing device, a fingerprint processing method, and a program capable of quickly performing matching without specifying the center of a fingerprint can be provided.

REFERENCE SIGNS LIST

1 Fingerprint processing device
2 Fingerprint reader
3 Database
11 CPU
12 RAM
13 ROM
14 SSD
15 Communication module
16 Display screen
17 IF (interface)
21 Image acquisition unit
22 Clarity determination unit
23 Ridge line quality determination unit
24 Feature point detection unit
25 Match processing unit

The invention claimed is:

1. A fingerprint processing device comprising:
at least one memory configured to store instructions; and
at least one processor configured to execute the instructions to:
calculate, for each of a plurality of feature points specified in a fingerprint image of a matching source, a representativeness based on a value obtained by multiplying a second degree and a first degree, the first degree representing that a first distance from the feature point to a pixel region having an image clarity in the fingerprint image less than a threshold corresponding to unclear image clarity, the second degree representing a smallest distance among second distances from the feature point to other of the feature points; and determine representative feature points used in match processing of the fingerprint from among the feature points, by selecting a predetermined number of the feature points in descending order of the calculated representativeness.

2. The fingerprint processing device according to claim 1, wherein the at least one processor is configured to execute the instructions to:

calculate, for each feature point, the representativeness by further using a degree of stability of a ridge line in pixels that correspond to the feature points.

3. The fingerprint processing device according to claim 1, wherein the at least one processor is configured to execute the instructions to:

perform the match processing using the determined representative feature points and a plurality of representative feature points in a fingerprint image of a matching destination.

4. The fingerprint processing device according to claim 1, wherein the at least one processor is configured to execute the instructions to:

specify, for each representative feature point, a representative extension direction of a ridge line of the fingerprint extending from the representative feature point, and assign a feature amount determined based on a distance from the representative feature point to a neighboring feature point, an extension direction referenced to the representative extension direction of the ridge line extending from the neighboring feature point, and the representativeness of the neighboring feature point; and perform the match processing of the fingerprint, using the feature amount assigned to each representative feature point, based on the representative feature points in the fingerprint image of the matching source and a plurality of representative feature points in the fingerprint image of a matching destination.

5. The fingerprint processing device according to claim 4, wherein for each representative feature point, the neighboring feature point neighbors the representative feature point in each of eight quadrant regions referenced to the representative extension direction of the and having the representative feature point as an origin.

6. The fingerprint processing device according to claim 1, wherein the at least one processor is configured to execute the instructions to:

specify, for each representative feature point, a representative extension direction of a ridge line of the fingerprint extending from the representative feature point, generate a ridge line extension direction determination image that includes a pixel value of a neighboring feature point indicating that a degree of matching between an extension direction referenced to the representative extension direction of the ridge line extending from the neighboring feature point and the specified representative extension direction is greater than a first threshold, and a pixel value of the neighboring feature point indicating that the degree of matching is less than a second threshold, and assign a feature amount representing a plurality of pixel values at predetermined positions referenced to the position of the representative feature point in the generated ridge line extension direction determination image; and perform the match processing of the fingerprint, using the feature amount assigned to each representative feature point, based on the representative feature points in the fingerprint image of the matching source and a plurality of representative feature points in the fingerprint image of a matching destination.

7. A fingerprint processing method performed by a processor and comprising:

calculating, for each of a plurality of feature points specified in a fingerprint image of a matching source, a representativeness based on a value obtained by multiplying a second degree and a first degree, the first degree representing that a first distance from the feature point to a pixel region having an image clarity in the fingerprint image less than a threshold corresponding to unclear image clarity, the second degree representing a smallest distance among second distances from the feature point to other of the feature points; and determining representative feature points used in match processing of the fingerprint from among the feature points, by selecting a predetermined number of the feature points in descending order of the calculated representativeness.

8. A non-transitory computer-readable recording medium storing a program that causes a computer to execute processes comprising:

calculating, for each of a plurality of feature points specified in a fingerprint image of a matching source, a representativeness based on a value obtained by multiplying a second degree and a first degree, the first degree representing that a first distance from the feature point to a pixel region having an image clarity in the fingerprint image less than a threshold corresponding to unclear image clarity, the second degree representing a smallest distance among second distances from the feature point to other of the feature points; and determining representative feature points used in match processing of the fingerprint from among the feature points, by selecting a predetermined number of the feature points in descending order of the calculated representativeness.

\* \* \* \* \*